United States Patent
Hiltebrandt

(12) 
(10) Patent No.: US 7,105,003 B2
(45) Date of Patent: Sep. 12, 2006

(54) SURGICAL INSTRUMENT

(75) Inventor: Siegfried Hiltebrandt, Knittlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 10/267,114

(22) Filed: Oct. 9, 2002

(65) Prior Publication Data

US 2003/0032970 A1 Feb. 13, 2003

Related U.S. Application Data

(63) Continuation of application No. 09/621,870, filed on Sep. 15, 1999, now abandoned.

(30) Foreign Application Priority Data

Sep. 17, 1998 (EP) .......................................... 98810930

(51) Int. Cl.
*A61B 17/22* (2006.01)

(52) U.S. Cl. ....................... 606/159; 606/170
(58) Field of Classification Search ................ 606/159, 606/170, 171, 174, 169, 180; 604/22
See application file for complete search history.

(56) References Cited

U.S. PATENT DOCUMENTS 5,833,692 A * 11/1998 Cesarini et al. ............. 606/170
6,656,195 B1 * 12/2003 Peters et al. ................. 606/159

* cited by examiner

Primary Examiner—Kevin T. Truong
(74) Attorney, Agent, or Firm—Paul Vincent

(57) ABSTRACT

A surgical instrument (1) for the removal of tissue comprises an outer tube (2) having an opening (22) for the removal of tissue, fashioned in a distal region, preferentially in the vicinity of the distal end of the outer tube (2). It further comprises an inner tube (3) disposed in the outer tube (2) and having a rigid proximal region for transferring forces or momenta acting on this proximal region to a distal region of the inner tube (3), preferentially to the distal end of the inner tube (3). The instrument further comprises a cutting tool (4) disposed at the distal region of the inner tube (3), preferentially at the distal end of the inner tube (3), for facilitating cutting of tissue which is subjected to the action of the cutting tool (4) in the vicinity of the opening (22) in the distal region of the outer tube (2), wherein the inner tube (3) has a flexible region (31) located between its rigid proximal region and the cutting tool (4). The inner tube (3) has a slit (5, 5a) in its wall in the flexible region (31) which, as viewed in the longitudinal direction of the inner tube (3) winds in a helical fashion about the longitudinal axis (L) of the inner tube (3) and meanders back and forth with respect to this helical line (52, 52a).

9 Claims, 3 Drawing Sheets

SURGICAL INSTRUMENT

This is a continuation of application number 09/621,870 filed Sep. 15, 1999 now abandoned and also claims Paris Convention priority of EP 98 810 930.2 filed Sep. 17, 1998 the entire disclosure of which are hereby incorporated by reference.

BACKGROUND OF THE INVENTION

The invention concerns a surgical instrument for the removal of tissue, comprising an outer tube having an opening, for accepting tissue, in a distal region, preferentially in the vicinity of the distal end of the outer tube and with an inner tube disposed within the outer tube and having a rigid proximal region for transmitting forces or momenta acting on this proximal region to a distal region of the inner tube, preferentially to the distal end of the inner tube, and also with a cutting tool disposed at the distal region of the inner tube, preferentially on the distal end of the inner tube, for cutting tissue subjected to the influence of the cutting tool in the vicinity of the opening of the distal region of the outer tube, wherein the inner tube comprises a flexible region between its rigid proximal region and the cutting tool.

Instruments of the kind categorizing the invention are available in innumerable embodiments. Instruments, as used in the area of endoscopy and in particular in the area of arthroscopy typically have an outer tube having an opening in the distal region, frequently in the vicinity of the distal end of the outer tube, into which tissue can be accepted. An inner tube is disposed in the outer tube having a cutting tool disposed in a distal region, frequently at the distal end of the inner tube. The cutting tool can be directly formed onto the inner tube or can be a separately manufactured component which is connected to the inner tube e.g. by means of welding. The cutting tool can be used to separate out tissue at the location of use by rotating the inner tube relative to the outer tube. The removed tissue is then suctioned-off, together with rinsing liquid normally used in this type of operation, with the assistance of vacuum and passed through the inner tube.

With typical (linearly extending) instruments used in the art of endoscopy and in particular in the field of arthroscopy, it is however sometimes difficult or even impossible for the surgeon to move the cutting tool to the desired location (e.g. the lower side of the patella, the upper and lower regions of the femurcondyle or portions of the crescent-shaped menisci, in particular the front and back horns thereof) at which cutting of the tissue should be carried out. The term "tissue" herein refers to any kind of tissue, i.e. soft tissue, tissue of intermediate hardness (e.g. cartilage) or even very hard tissue (e.g. bone tissue). The term "cutting" accordingly refers to all conventional means of removal in this art, e.g. in particular cutting, milling etc.

In order to simplify advancement towards these locations which are not accessible or are at best accessible only with difficulty, other kinds of instruments are available which deviate from the typical linear shape, e.g. those in which the instrument is angled in the distal region. With the assistance of such instruments, it is easier to gain access to locations which are not accessible or are accessible only with great difficulty using the conventional linearly designed instruments.

It is immediately obvious that, when using such Instruments having a non-linear shape, the rigid proximal component of the inner tube must transfer the driving force or the driving momentum to the cutting tool disposed at the distal region, preferentially on the distal end. However, towards this end, one must pass through the non-linear transitional region between the proximal portion of the inner tube and the cutting tool. In other words, the Inner tube must transfer the driving force or the driving momentum past the non-linear transitional region to the cutting tool.

Towards this end, e.g. an instrument is described in EP-A-0,445,918 having a flexible transition region disposed between the rigid proximal region and the distal region. This flexible transitional region is configured in such a fashion that a plurality of discrete openings are provided at this location in such a fashion that the diameter of the inner tube is alternately reduced in the horizontal and vertical directions, each perpendicular to the longitudinal axis of the inner tube, so that only bridge regions are present in these locations, wherein neighboring bridges are however connected to each other.

The mutually connected bridges guarantee the flexibility of the inner tube in the transitional region while nevertheless facilitating a transfer of forces or momenta to the distally disposed cutting tool. However, the forces or momenta which can be transferred with a flexible transitional region of this kind are somewhat limited. The limitation of the forces or momenta which can be transferred to the cutting tool is also the intended purpose of this design, since the bridges also serve as intended breaking locations. Should the forces or momenta acting on the cutting tool exceed a predetermined limiting value, the bridges break. One thereby prevents the introduction of extremely large forces or momenta onto the cutting tool which could fracture same, wherein individual broken pieces of the cutting tool could gain entrance to the location of the operation and into the tissue.

As already mentioned, the forces or momenta which are to be transferred are limited. Precisely for the case of alternating loads which, for example, occur during oscillating operation of such instruments (continuous change of the rotation direction of the inner tube relative to the outer tube), the bridges can be quickly broken. On the other hand, oscillating operation is an optional mode of operation for an instrument of this type which is extremely useful, since precisely for tissue having intermediate hardness and for hard tissue it is often not possible to predict which rotational direction is suitable for removal of the tissue. This depends in part on the geometrical configuration of the tissue to be removed and on the direction from which one gains entrance to the tissue to be removed. In some of such cases, one can effect removal of the tissue using oscillating operation of the instrument, which would be difficult or even impossible using operation in only one single rotational direction. However, this necessitates transmission of the alternating load from the proximal region of the inner tube to the cutting tool.

It is therefore the purpose of the invention to propose an instrument having an inner tube with a flexible region, which can also be used with non-linear instruments, wherein the flexible region of the inner tube should have a sufficient degree of alternating load strength to be able to withstand the alternating loads during oscillating operation. Moreover, the inner tube should be easy to manufacture, since it is also a purpose of the invention to propose a tube per se, having a flexible region with sufficient strength with respect to alternating loads for withstanding same. Clearly, the inner tube itself must also be sufficiently leak-tight in precisely this flexible region such that the suctioned off tissue portions cannot escape out of the inner tube.

SUMMARY OF THE INVENTION

This purpose is achieved with an instrument in accordance with the invention, in that the inner tube has a slit in its wall at the flexible region which, as seen in the longitudinal direction of the inner tube, winds in a helical path about the longitudinal axis of the inner tube and meanders back and forth with respect to this helical path. In particular, a surgical instrument for the removal of tissue has an outer tube having an opening for the acceptance of tissue in a distal region thereof, preferentially in the vicinity of the distal end of the outer tube. In addition, the instrument comprises an inner tube disposed within the outer tube and a rigid proximal region to transfer forces or momenta acting on this proximal region to a distal region of the inner tube, preferentially to the distal end of the inner tube. In addition, the instrument comprises a cutting tool disposed at the distal region of the inner tube, preferentially on the distal end of the inner tube, in order to cut tissue subjected to the cutting tool in the vicinity of the opening of the distal region of the outer tube. The inner tube has a flexible region between its rigid proximal region and the cutting tool. The inner tube has a slit in its wall at the flexible region which, as viewed in the longitudinal direction of the inner tube, winds in a helical path about the longitudinal axis of this inner tube, and meanders back and forth about this helical line. This configuration gives the necessary strength with respect to alternating loads while maintaining the necessary flexibility. The terms "cutting" and "cutting tool" are intended, as already mentioned above, to include all of the usual types of tissue removal in this art, in particular cutting, milling and the like and tools performing these acts such as cutting tools, milling tools etc.

In an embodiment of the instrument, the meandering slits define alternating teeth and recesses, wherein each recess has an associated tooth and each tooth is disposed within a recess. The teeth and the recesses are shaped in such a fashion that an axial slippage of a tooth out of a recess is impossible. Even in the event of instruments having an angled distal region with which the flexible region is necessarily separated in an axial direction, the teeth thereby always remain in engagement with the corresponding recess during rotation of the inner tube so that the forces or the momenta are securely transmitted to the cutting tool.

An additional configuration is distinguished in that the opening provided in the outer tube for acceptance of the tissue is disposed in the distal end region of the outer tube and the cutting tool is disposed on the distal end of the inner tube. In principle, the opening can also be provided at a location other than the distal end of the outer tube. The case in which the opening is provided at the distal end of the outer tube is however the most frequent one, since, if possible, one would like to insert the instrument to as shallow a depth as possible into the body of the patient or his or her joint.

The width of the slit in the wall of the inner tube can e.g. lie in the range between approximately 0.05 mm to approximately 1 mm and the thickness of the wall of the inner tube can lie in the range of approximately 0.1 mm to approximately 0.7 mm, in particular, in the range of approximately 0.15 mm to approximately 0.5 mm.

The pitch of the helical path along which the slit provided in the wall of the inner tube can e.g. lie in the range between approximately 0.5 mm/winding to approximately 4 mm/winding.

The cutting tool can be a separately manufactured element which is connected to the distal end of the inner tube. This facilitates a separate manufacture of the cutting tool and the inner tube to simplify manufacture while nevertheless allowing the cutting tool and the inner tube to be reliably connected to each other, e.g. by means of welding to guarantee transfer of the forces or momenta onto the cutting tool. Alternatively, the cutting tool and the inner tube can be produced as an integral, single piece.

In an additional embodiment, the outer tube can extend linearly in the proximal region, whereas the distal region of the outward tube at which the cutting tool is disposed can be configured to deviate from the straight line determined by the proximal region ("angled off"). In this case, the inner tube is configured in such a fashion that the flexible region of the inner tube is disposed in the transitional region between the proximal and distal portions of the outer tube.

The distal region of the outer tube itself can thereby be configured in a linear fashion. The flexible region of the inner tube is disposed at the transitional region where the proximal region and the distal region meet.

An additional independent aspect of the invention concerns a tube (e.g. the inner tube mentioned above in connection with the instrument) having a rigid proximal region and a flexible region disposed distally with respect to the rigid proximal region. The flexible region of the tube has a slit in its wall which, as viewed in the longitudinal direction of the tube, winds in a helical fashion about the longitudinal axis of the tube and meanders with respect to this helical line. This tube has advantages corresponding to those already mentioned in connection with the instrument (strength with respect to alternating loads, leak tightness, secure transmission of the necessary forces and momenta).

The meandering slit defines alternating teeth and recesses, wherein each recess has an associated tooth and each tooth is disposed in a recess and the teeth and the recesses have a shape which prevents an axial slipping of the teeth out of the recesses.

The width of the slit in the wall of the tube can lie in a range between 0.05 mm to approximately 1 mm, the tube wall thickness can be in the range between approximately 0.1 mm to approximately 0.7 mm, and in particular in a range between approximately 0.15 mm to approximately 0.5 mm.

The pitch of the helical line along which the slit provided in the wall of the inner tube extends can lie in a range between approximately 0.5 mm/winding and approximately 4.0 mm/winding.

The invention is described more closely below with regard to the drawings, partially in schematic representation and/or in section.

DESCRIPTION OF THE PREFERRED EMBODIMENT

Figure 1:
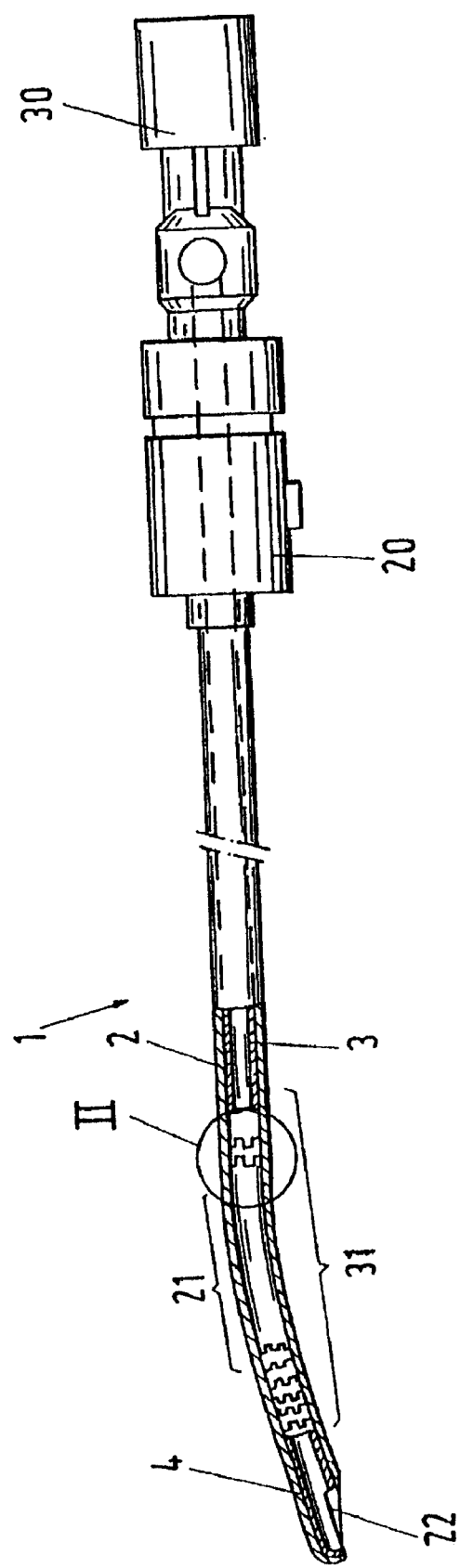
FIG. 1 shows an embodiment of a surgical instrument in accordance with the invention in an assembled state.

FIG. 1 shows an embodiment of a surgical instrument 1 in accordance with the invention. The instrument 1 clearly comprises an outer tube 2 in which an inner tube 3 is disposed for rotation. The surgical instrument 1 can be accepted by a handle (not shown) in which a rotating drive, e.g. an electrical motor, can be provided for rotational drive of the inner tube 3. The proximal end of the inner tube is firmly connected to a coupling member 30 for coupling to the rotating drive by bringing the coupling member 30 into engagement therewith. The proximal end of the outer tube 2 is firmly connected to a locking member 20 which, in turn, can be accepted by and locked within the handle (not shown). The coupling member 30 and the inner tube 3 connected thereto can be rotated relative to the locking member 20 and relative to the outer tube 2 connected thereto.

The proximal region of the inner tube extends in a rigid manner from the proximal end region towards a flexible region 31. This flexible region 31 of the inner tube 3 extends past curved region 21 of the outer tube 2 substantially up to a cutting tool 4 which is connected to the distal end of the inner tube 3. The cutting tool 4 can be a separately manufactured element which is subsequently connected to the inner tube 3 using an appropriate connecting technique e.g. by means of welding. Alternatively, the cutting tool 4 and the inner tube 3 can be integral, that is to say, made from a single piece. The designation "cutting" and "cutting tool" refer, as already mentioned a plurality of times above, to all types of removal processes conventional in this art such as e.g. cutting, milling and the like as well as to the associated tools e.g. cutting tools, milling tools and the like. The cutting tool 4 can remove tissue which can be accepted into an opening 22 at the distal end of the outer tube 2. The tissue removed in this fashion can be suctioned through the inside of the inner tube 3. One thereby guarantees, as will be further described below, that the removed tissue which has been suctioned into the inner tube 3 does not escape out of the inside region of the inner tube 3. In addition, the manner in which the flexible region 31 is configured guarantees that the forces and momenta occurring during oscillating operation are securely transmitted to the cutting tool 4, wherein the flexible region 31 has an alternating load strength which is sufficient therefor.

Figure 2:
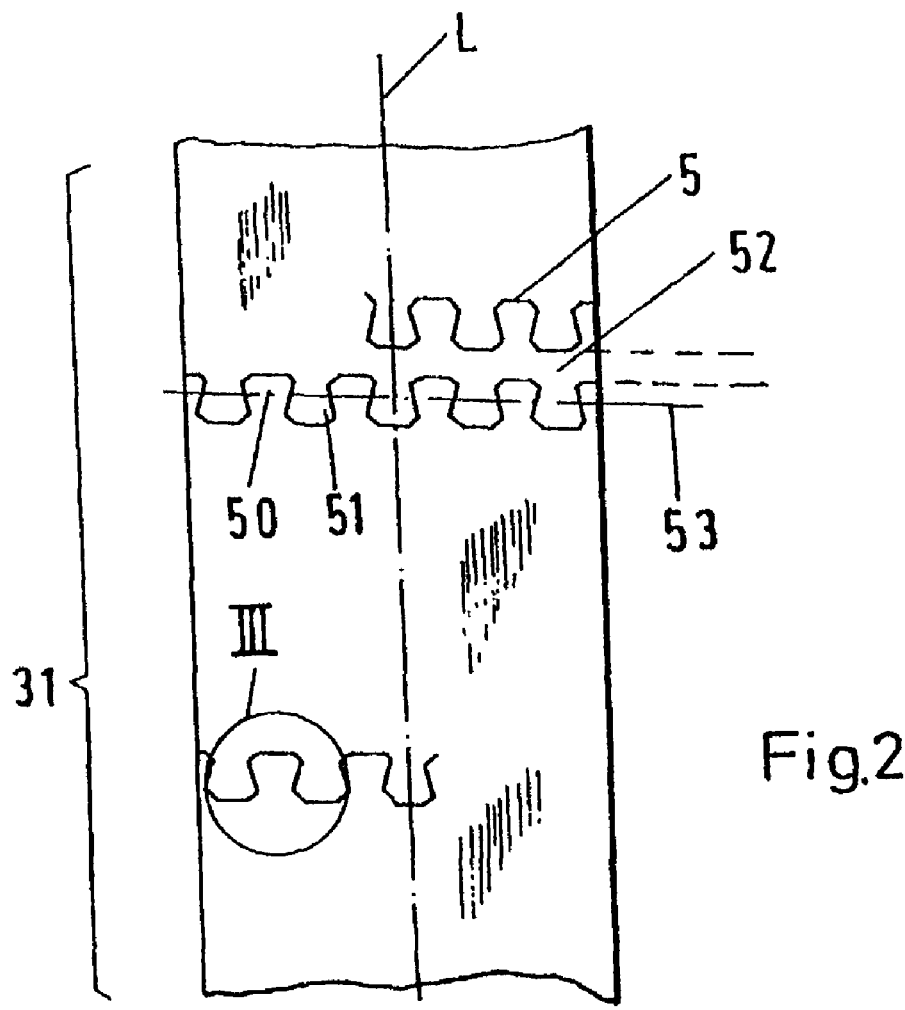
FIG. 2 shows the section II of the flexible region of the inner tube of FIG. 1.
Figure 3:
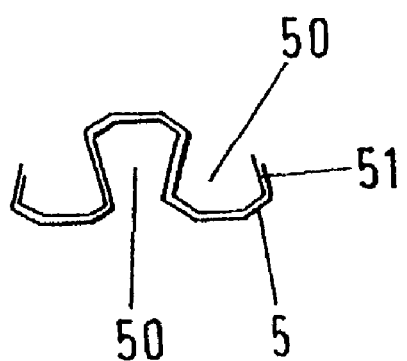
FIG. 3 shows the section III of the flexible region of FIG. 2.

FIG. 2 shows the section II of the flexible region 31 of the inner tube 3 in an enlarged, unfolded representation. FIG. 3 shows an enlarged section of FIG. 2. As seen in FIG. 2, a slit 5 is provided for in the wall of the inner tube 3 which winds about the longitudinal axis L of the inner tube 3 in a helical fashion. (Although the slit is not shown in the drawing along the entire length of FIG. 2, it is in fact disposed along the entire region 31). The slit 5 meanders back and forth relative to the helical path. The meandering dependence of the slit 5 defines alternating teeth 50 and recesses 51. A tooth 50 projects into each of the recesses 51 formed by the slits 5. Inspection of two slits disposed one above the other, leads to observation of a bridge 52 formed between these two slits. Teeth extend axially away from this bridge in an alternating fashion in the upper and in the lower directions and project into corresponding recesses 51. Each tooth 50 and recess 51 thereby has a shape which prevents an axial slippage of the tooth out of a recess 51. Clearly, for curved (angled) instruments in accordance with FIG. 1, the flexible region 31 of the inner tube 3 is subjected to a tensile load. The slit 5 must therefore be configured in such a fashion that the teeth 50 and recesses formed thereby wind through the curved region 21 of the outer tube 2 while facilitating transmission of the necessary forces or momenta to the cutting tool 4 while, in particular, having the necessary alternating load strength required for oscillating operation.

In a typical embodiment, the thickness of the inner tube 3 wall lies in the range between approximately 0.1 mm to approximately 0.7 mm, in particular in the range between approximately 0.15 mm to approximately 0.5 mm. The width of the slit 5 can lie in the range between approximately 0.05 mm to approximately 1 mm. The width of the slit can thereby change along its travel and must not be constant along every portion thereof. The helical path 53 of the slit 5 along which the meandering slit 5 extends can e.g. have a pitch lying in a range between approximately 0.5 mm/winding to approximately 4 mm/winding (similar to the pitch of a thread) and, in particular, assume values of approximately 0.9 mm. The bridge 52 can e.g. have a width of approximately 0.3 mm. The entire inner tube 3 can have a diameter of approximately 3 mm. Clearly, these values are only to be considered as examples and can be adjusted to the appropriate requirements and conditions.

An inner tube 3 configured in this fashion can be used to suction-off tissue components, removed with the assistance of a cutting tool 4, along with a rinsing liquid through the inner region of the inner tube 3 without having the tissue components pass through the slit 5 to gain entrance to the region between the inner tube 3 and the outer tube 2 which could lead to seizing of the inner tube 3 within the outer tube 2.

Figure 4:
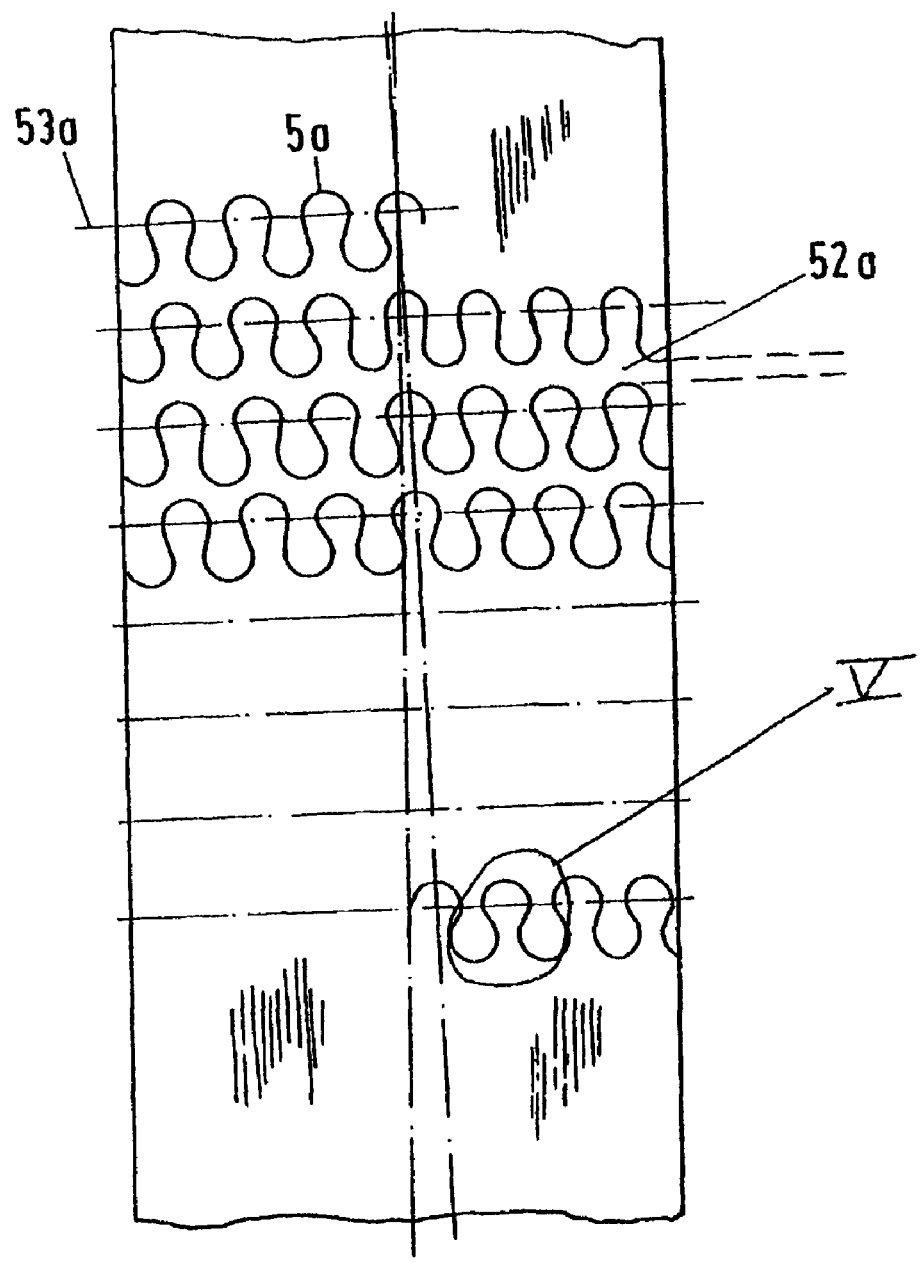
FIG. 4 shows a section of another embodiment of the flexible region.
Figure 5:
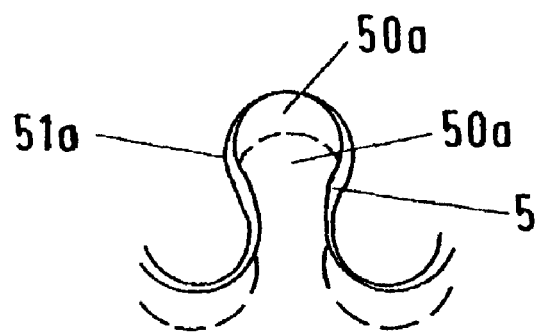
FIG. 5 shows the section V of the flexible region of FIG. 4.

Another embodiment of the flexible region is shown in FIG. 4 in an unfolded representation. FIG. 5 shows an enlargement of section V of FIG. 4. The reference symbols in FIG. 3 and FIG. 4 have been maintained with only the letter "a" being added. As seen in FIG. 4, the travel of the slit 5a along the helical path 53a has a different orientation than that of FIG. 3 (similar to a right-handed thread, whereas the helical line 53 in FIG. 3 travels like a left-handed thread). The shape of the teeth 50a and the recesses 51a has changed from a "square" configuration (FIG. 2 and FIG. 3) to a "rounded" configuration. A slippage of the tooth 50a out of a recess 51a is still prevented. This can be particularly clearly seen in FIG. 5, wherein the tooth 50a is disposed in the recess 51a with (dashed lines) and without (solid lines) tensile loading. For the case of tensile loading (dashed lines) which is normally the case for instruments having a curved outer tube transitional region between the proximal and distal regions, the tooth 50a securely seats sidewardly on the recess 51. Without tensile loading (solid lines) a small amount of play (namely the width of the slit at the corresponding location) remains. One can also easily see in FIG. 5 that the width of the slit can vary along the slit 5a. The slit is thereby significantly wider in the side region than at the head end.

Clearly, there are a plurality of additional possibilities for the travel of the meandering slit. It is only important that the teeth formed thereby do not slip, in the axial direction, out of their associated recesses. The shape of the teeth and of the recesses as well as the other parameters such as the pitch of the helical path, the width of the bridge, the width of the slit and its variation along the slit etc. can each be adapted to the respective requirements. This can, in particular, depend on the type of tissue which the cutting tool should remove (soft tissue, tissue of intermediate hardness, or very hard tissue). Clearly, the type of removal procedure (cutting, milling and the like) can also be adjusted to the respective tissue by choosing an instrument having an appropriate cutting tool.

What is claimed is:

1. A surgical instrument for the removal of tissue, the instrument comprising:
   an outer tube having an opening in a distal region thereof for accepting the tissue;
   an inner tube disposed within said outer tube, said inner tube having a rigid proximal region for transmitting forces or momenta acting on said inner tube proximal region to a distal region of said inner tube, said inner tube having a flexible region between said inner tube proximal region and said inner tube distal region, said inner tube comprising a wall in said flexible region, said wall having a slit in said flexible region, said slit winding in a helical path about a longitudinal axis of said inner tube, said slit meandering back and forth with respect to said helical path, wherein said meandering slit defines alternating teeth and recesses, each recess having an associated tooth and each tooth being disposed in a recess, said teeth and said recesses having a shape which prohibits an axial slippage of said teeth out of said recesses, wherein said slit has a width of less than approximately 1 mm and said wall of said inner tube has a thickness between approximately 0.1 mm to approximately 0.7 mm, with said helical path having a pitch of more than approximately 0.5 mm/winding; and a cutting tool disposed at said distal region of said inner tube for cutting the tissue subjected to an influence of said cutting tool in a vicinity of said opening in said distal region of said outer tube.

2. The instrument of claim 1, wherein said opening in said outer tube for acceptance of the tissue is disposed in a distal end region of said outer tube, and wherein said cutting tool is disposed at a distal end of said inner tube.

3. The instrument of claim 1, wherein said thickness is between approximately 0.15 mm to approximately 0.5 mm.

4. The instrument of claim 1, further comprising means for connecting said cutting tool to said distal region of said inner tube.

5. The instrument of claim 1, wherein said cutting tool is integral with said inner tube.

6. The instrument of claim 1, wherein said outer tube extends in a linear fashion in a proximal region of said outer tube, and wherein said cutting tool is disposed in said distal region of said outer tube, said outer tube distal region displaced from a line defined by said proximal region of said outer tube, wherein said flexible region of said inner tube is disposed in a transitional region extending between and joining said outer tube proximal region and said outer tube distal region.

7. The instrument of claim 6, wherein said outer tube distal region extends in a linear fashion.

8. A tube, comprising:
a rigid proximal region;
a distal region; and
a flexible region disposed between and connecting said rigid proximal region and said distal region, said flexible region with a tube wall having a slit, said slit winding in a helical path about a longitudinal axis of said tube and meandering back and forth with respect to said helical path, wherein said meandering slit defines alternating teeth and recesses, wherein each recess has an associated tooth and each tooth is disposed in a recess, said teeth and said recesses having a shape which prohibits an axial slippage of said teeth out of said recesses, wherein said slit has a width of less than approximately 1 mm and said wall of said tube has a thickness between approximately 0.1 mm to approximately 0.7 mm, with said helical path having a pitch of more than approximately 0.5 mm/winding.

9. The tube of claim 8, wherein said thickness is between approximately 0.15 mm to approximately 0.5 mm.

* * * * *